United States Patent [19]

Arbaczawski

[11] 4,397,322

[45] Aug. 9, 1983

[54] NON-SUDSING SHAMPOO AND CONDITIONER COMPOSITION

[76] Inventor: Joseph Arbaczawski, 1752 Colonial South Dr., Conyers, Ga. 30208

[21] Appl. No.: 144,779

[22] Filed: Apr. 28, 1980

[51] Int. Cl.$^3$ .............................................. A45D 7/00
[52] U.S. Cl. .......................................... 132/7; 424/70
[58] Field of Search ............... 424/70, 71, 62, DIG. 2; 526/307; 132/7; 252/542

[56] References Cited

U.S. PATENT DOCUMENTS

| | | | |
|---|---|---|---|
| 3,341,319 | 9/1967 | Hibbard | 252/542 |
| 3,412,019 | 11/1968 | Hoover et al. | 526/307 |
| 3,489,686 | 1/1970 | Parran | 252/542 |
| 3,496,110 | 2/1970 | Shumway | 252/542 |
| 3,715,428 | 2/1973 | Quasius | 132/7 |
| 3,959,463 | 5/1976 | Nersesian et al. | 424/362 |
| 3,996,146 | 12/1976 | Tarasov et al. | 424/70 |
| 4,027,008 | 5/1977 | Sokol | 424/62 |
| 4,201,766 | 5/1980 | Grollier et al. | 424/71 |
| 4,213,960 | 7/1980 | Grollier et al. | 424/70 |
| 4,299,817 | 11/1981 | Hannan | 424/70 |

OTHER PUBLICATIONS

Harry's Cosmeticology, 6th Ed., vol. I (1974), published by Leonard Hill Books, pp. 244,248,378–383,611,613,616,617,730,731 & 732.

*Primary Examiner*—Gregory E. McNeill
*Attorney, Agent, or Firm*—Newton, Hopkins & Ormsby

[57] ABSTRACT

A composition, having an organic, water soluble cationic, polyelectrolyte and a hydrophilic thickener dispersed in water for providing a viscosity of about 1400 centipose per second and a pH adjusted to about 5.6, is employed as a non-sudsing shampoo for washing the hair of a person in a pool, spa or hot tub, the composition serving the function of also flocculating for facilitating the capture in the filter system of the occluded dirt and oil from the hair for thereby clarifying the water in such pool, spa or hot tub.

4 Claims, No Drawings

NON-SUDSING SHAMPOO AND CONDITIONER COMPOSITION

BACKGROUND OF THE INVENTION

1. Field of the Invention

This invention relates to a non-sudsing shampoo and conditioner composition and is more particularly concerned with a non-sudsing shampoo and a process of using the same in conjunction with a recirculating water system.

2. Description of the Prior Art

In the past, the use of polyelectrolytes has been disclosed in U.S. Pat. Nos. 3,980,769; 4,048,309; 3,996,146 and 4,009,256. The hair cleansing ability of such polyelectrolytes has not, however, been recognized nor has the usefulness for cleaning the person's hair in a hot tub been recognized.

3. Brief Description of the Invention

Briefly described, the present invention includes a composition having an organic water soluble cationic polyelectrolyte and a hydrophilic thickener dispersed in water for providing a viscosity between about 100 centipoise per second to a gel and preferably about 1400 cps. The pH is adjusted to between pH 3.5 and pH 6.5. The composition is utilized, full strength, for washing the hair of a person while the person is in a swimming pool, spa or hot tub. The composition readily removes dirt and oil from the hair when the hair is rinsed in the water; however, the composition has a flocculating effect which enables it to occlude the dirt and oil, remove it from the hair and agglomerate it with the composition so that this mixture is retained in the filters of the pool, spa or hot tub or is deposited along the sides of the vessel where the mixture is wiped away with a sponge or cloth.

Accordingly, it is an object of the present invention to provide a unique hair shampoo and conditioning composition for use by a person in a filtered recirculating water system where foam would be deleterious to the system and aesthetically displeasing to the occupants of the system.

Another object of the present invention is to provide an unique hair shampoo and conditioning formulation that, when used, thoroughly cleans the hair to a squeaky clean condition and reduces tangles, snags and the usual discomforts associated with the combing of freshly shampooed hair.

Another object of the present invention is to provide a hair shampoo and conditioning composition which, when used, will impart to the hair an improved luster and manageability.

Another object of the present invention is to provide a hair shampoo and conditioning composition which, when used, in a water recirculation system clarifies the water coagulates or agglomerates dirt and oil from the hair and in the water so that it can be easily and efficiently filtered or otherwise removed.

DESCRIPTION OF THE PREFERRED EMBODIMENT

In more detail, the non-sudsing hair shampoo and conditioner of the present invention includes an admixture of a high molecular weight organic, water soluble, cationic, polyelectrolyte and a hydrophilic thickener in water, this admixture having at least a viscosity of 100 centipose per second (cps) and preferably a viscosity of about 1400 centipose per second. The polyelectrolytes useful in this sudless shampoo composition include the high molecular weight water soluble amino and quaternary ammonium homopolymers or copolymers derived from dimethyl diallyl ammonium salts. Such amino and quaternary polymers derived from dimethyl diallyl ammonium salts have a molecular weight between 20,000 and 3,000,000 with a molecular chain containing the units of one or both of the following formulas:

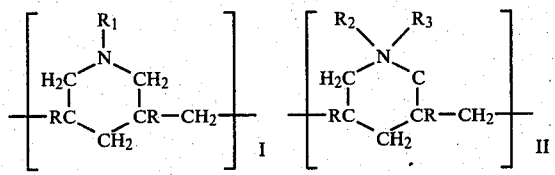

wherein R is hydrogen methyl; $R_1$, is hydrogen, or an alkyl group having one to 22 carbon atoms, or a lower hydroxyalkl group having one to five carbon atoms, or a lower alkyl group containing a terminal amido group, such as beta-propionamido; and where $R_2$ and $R_3$ are independently alkyl groups having one to 22 carbon atoms, lower hydroxyalkyl groups having one to five carbon atoms, and lower alkyl groups containing terminal amido groups, such as beta-propionamido; and where $R_2$ and $R_3$ together with N (nitrogen) form piperidinyl or morphinyl groups.

Examples of suitable organic anions for polymization with the quaternary cationic groups include acetate, borate, bromide, chloride, citrate, tartrate, bisulfate, bisulfite, sulfate, phosphate, and succinate. The homopolymers and copolymers of Formula I are described in Butler et al., U.S. Pat. No. 2,926,161. The homopolymers and copolymers of Formula II are described in U.S. Pat. Nos. 3,288,770 and 3,412,019.

An especially appropriate homopolymer of this type with a molecular weight less than 100,000 is marketed commercially as a 40% aqueous solution under the trademark MERQUAT 100 by Merek & Co., Inc., Rahway, N.J.

Acrylamide and diacetone acrylamide can be formed into copolymers containing units of Formula I or II. A particularly suitable quaternary copolymer formed from dimethyl diallyl ammonium chloride and an acrylamide is sold under the name of MERQUAT 550 by Merek & Co., Inc., Rahway, N.J. MERQUAT 550 is an 8% aqueous solution of a copolymer having an average molecular weight of more than 500,000.

The water soluble polyamide-epichlorohydrin resins as described in French Patent No. 1,570,656 are further examples of polyelectrolytes useful in the present invention. Commercially available resins of this type are marketed under the trademark CARTARETIN by the Sandoz-Wander Corporation, Hanover, N.J. These resins have a nitrogen content of 17.0–18.0% on a dry basis and a viscosity, in 30% by weight aqueous solution, of 350 to 800 cps at 20 degrees C.

The copolymers of acrylamide and quaternary ammonium compounds especially acrylamide (beta-methacryloyloxyethyl) trimethylammonium methyl sulfate as described in U.S. Pat. No. 3,480,541 (1969) are still further examples of polyelectrolytes useful in the present invention. Viscosities of 1% aqueous solutions of these copolymers are between 600 and 1200 cps at 20 degrees C. They are commercially marketed under the trademark RETEN by Hercules, Inc., Wilmington, Del.

A particularly preferred polymer is polydimethyldiallyl ammonium chloride at a concentration of from 0.01% to up to 40% by weight based on the total weight of the formulation at a pH range of from 3.5 to 9.0.

The unique mechanism of this invention is the ability of the organic cationic polyelectrolyte to cause destabilization of suspensions, mainly by the reduction of the elctrokinetic potential of the surfaces of the dirt and grease or oil particles, while acting as a bridging mechanism for the polymer chains. This enables the occluding of the dirt and grease particles in the shampoo so as to remove them from the hair when my shampoo is used.

The hydrophilic thickener of the composition is employed to lubricate the hair and to simulate the feeling of lather. Also the viscosity imparted by the thickener to the polyelectrolyte solution allows a more thorough contact of the electrolyte with the individual hair shafts so that, as the fingers mechanically massage the formulation into the hair, the dirt is captured while the oil is emulsified within the coating of thickened water and the polyelectrolyte surrounding the hair shaft. When the hair is rinsed and washed out, the formulation, containing the dirt and oil, is flocculated and coagulated by the action of the cationic organic polyelectrolyte in the water so that the filter of the water system is usually easily and efficiently able to remove the flocculant.

Examples of suitable thickeners which act as suspending agents in my shampoo formulations include hydroxylpropylmethyl cellulose, proteins, gelatin and methyl cellulose. Particularly effective thickeners are the nonionic water soluble cellulose polymers such as hydroxyethyl cellulose marketed under the trademark NATROSOL by Hercules, Inc., Wilmington, Del.

Viscosity of my hair shampoo, as applied to the hair, is usually critical to the "massagability" of the hair. At 100 cps the hair strands are coated sufficiently to reduce friction, allowing the hair and scalp to be easily and thoroughly massaged by the fingers. The "lather sensation" increases with the viscosity and by 1000–1500 cps the user of my composition gets the feeling of rich luxurious lather on the hair and scalp as the fingers massage. This sensation is important because its a typical "shampoo feeling" that everyone expects and is use to feeling. Conventionally the feeling is caused by lather. With my shampoo formulation, this feeling is uniquely simulated as a function of the viscosity in my composition even though no sudsing occurs. The simulation of the "lather sensation" is, therefore, a significant part of this invention.

The following is a list of cationic polyelectrolytes which are useful in my compositions:

I. Acrylic acid and methacrylic acid polymers
1. N-alkyl-substituted aminoalkyl esters of acrylic acids U.S. Pat. No. 3,171,805 (1965)
2. Poly(diethylaminoethylmethylacrylate) French Pat. No. 1,570,656 (1969)
3. Poly(diethylaminoethylacrylate) French Pat. No. 1,570,656 (1969)
4. Poly(dimethylaminoethylacrylate) U.S. Pat. No. 3,014,896 (1961)
5. Dimethylaminopropylacrylate U.S. Pat. No. 3,171,805 (1965)
6. Polymethacryloxyethyl sulfonium halide U.S. Pat. No. 3,332,835 (1967)
7. Copolymer of acrylamide and water soluble acid esters (e.g., methyl acid maleate) U.S. Pat. No. 3,201,304 (1965)
8. Copolymers of acrylamide and quaternary ammonium compounds U.S. Pat. No. 3,480,541 (1969)
9. Copolymers of acrylamide and diallylamine (or diallyammonium) compounds U.S. Pat. No. 3,171,805 (1965)
10. Vinyl lactam-acrylamide (or methacrylamide) copolymer (and/or hydrolyzed) U.S. Pat. No. 3,412,020 (1968)
11. Copolymer of diacetone acrylamide and various comonomers (e.g., substituted acrylamide, diallylammonium compounds) U.S. Pat. No. 3,489,681 (1970)
12. Carbamoyl polymers U.S. Pat. No. 3,539,535 (1970)
13. N-substituted-N'-dialkylaminoalkyl) acrylamides U.S. Pat. No. 3,171,805 (1965)
14. Condensation product of polyacrylamide and polyamine U.S. Pat. No. 3,503,946 (1970)
15. Crosslinked polyacrylamide U.S. Pat. No. 3,488,720 (1970)
16. Graft copolymers of acrylamide methylamine-epichlorhydrin U.S. Pat. No. 3,697,370 (1972)

II. Polyvinyl alcohol and its derivitives
1. Reaction product of polyvinyl alcohol, thiourea or an alkyl-substituted thiourea and a strong mineral acid U.S. Pat. No. 3,148,142 (1964)
2. Partially quaternized homopolymers of vinyl esters of a-halogenated aliphatic carboxylic acids or copolymers of vinyl esters of a-halogenated aliphatic carboxylic acids and other polymerized monomers (e.g., vinyl acetate, methyl methacrylate, styrene) in which some of the a-halo-carbozy groups are quaternized. British Pat. No. 1,073,823 (1967); U.S. Pat. No. 3,432,430 (1969)

III. Maleic acid and its anhydride
Polyimideamines U.S. Pat. No. 3,507,787

IV. Polyamines and related substances
1. Phosphoramide derivatives of polyamines U.S. Pat. No. 3,576,741 (1971)
2. Polyesteramines U.S. Pat. No. 3,715,335 (1973) and U.S. Pat. No. 3,470,136 (1969)
3. 2-Methylene-3-butenyl quaternary ammonium monomers and polymers U.S. Pat. No. 3,673,164 (1972 and U.S. Pat. No. 3,544,532 (1970)
4. Condensation products of polyalkylene polyamines and epoxyhalides U.S. Pat. No. 3,391,090 (1968)
5. Condensation products of alkylene polyamine and polyfunctional halohydrins (the alkylene polyamine polyfunctional halohydrin polymers) U.S. Pat. No. 3,741,891 (1973)
6. Poly-B-asparaginepolyalkylenepolyamine halohydrin resins U.S. Pat. No. 3,351,520 (1967)
7. Polymers from epichlorohydrin and methylamine U.S. Pat. No. 3,493,502 (1970); U.S. Pat. No. 3,567,659 (1971); and U.S. Pat. No. 3,697,370 (1972)

V. Alkylenimines(aziridines) Ethylene (alkylene) oxides
1. Polyalkylenimines U.S. Pat. No. 3,210,308 (1965); and U.S. Pat. No. 3,203,910 (1965)
2. Polyethylenimines U.S. Pat. No. 3,408,292 (1968)
3. Polymers from N-substituted ethylenimines and polyaziridinyl compounds U.S. Pat. No. 3,468,818 (1969)

4. Copolymers of ethylenimine and epichlorohydrin U.S. Pat. No. 3,294,723 (1966)
5. Substituted acylated polyimine resins U.S. Pat. No. 3,640,909 (1972)
6. Fluorinated copolymers of alkyl-enimines U.S. Pat. No. 3,341,476 (1967)
7. Acryloxyalkyoxalkylketimines and -aldimines, their polymers, their primary amine monomer and polymers U.S. Pat. No. 3,497,485 (1970)
8. Copolymers of alkylenimine U.S. Pat. No. 3,579,488 (1971)
9. Ethyleneimine (aziridine) compounds U.S. Pat. No. 3,498,932 (1970) and U.S. Pat. No. 3,752,854 (1973)

VI. Polyamides
1. Polymeric amide-dialkyl ammonium salt-paraformaldehyde U.S. Pat. No. 3,367,918 (1968)
2. Reaction product of sulfuric acid and allophane U.S. Pat. No. 3,535,259 (1970)

VII. Polystyrene
Poly(vinylbenzylsulfonium) halides U.S. Pat. No. 3,216,979 (1965)

VIII. Heterocylic polymers
1. Cyclic amidine polymers (heterocyclic polymers containing a cyclic amidine group in the main polymeric chain) U.S. Pat. No. 3,576,740 (1971); U.S. Pat. No. 3,450,646 (1969); and U.S. Pat. No. 3,509,046 (1970)
2. Polyvinyl pyrrolidone (crosslinked polyelectrolytes) U.S. Pat. No. 3,235,490 (1966)

IX. Polysulfones and polysulfines
1. Polymers of unsaturated sulfines U.S. Pat. No. 3,214,370 (1965)
2. High molecular weight polysulfones U.S. Pat. No. 3,308,102 (1967)

X. Polymers of diallylammonium (and diallyldialklammonium) salts
1. Modified polyamines (polyquaternary compounds), prepared by polymerizing a quaternary ammonium monomer or by alkylation of already formed polyamine compounds (polymers of polydialkyldiallyl ammonium salt) U.S. Pat. No. 3,288,770 (1966); U.S. Pat. No. 3,461,163 (1969); and U.S. Pat. No. 3,472,740 (1969).

VIII. Heterocylic polymers
1. Cyclic amidine polymers (heterocyclic polymers containing a cyclic amidine group in the main polymeric chain) U.S. Pat. No. 3,576,740 (1971); U.S. Pat. No. 3,450,646 (1969); and U.S. Pat. No. 3,509,046 (1970)
2. Polyvinyl pyrrolidone (crosslinked polyelectrolytes) U.S. Pat. No. 3,235,490 (1966)

IX. Polysulfones and polysulfines
1. Polymers of unsaturated sulfines U.S. Pat. No. 3,214,370 (1965)
2. High molecular weight polysulfones U.S. Pat. No. 3,308,102 (1967)

X. Polymers of diallylammonium (and diallyldialklammonium) salts
1. Modified polyamines (polyquaternary compounds), prepared by polymerizing a quaternary ammonium monomer or by alkylation of already formed polyamine compounds (polymers of polydialkyldiallyl ammonium salt) U.S. Pat. No. 3,288,770 (1966); U.S. Pat. No. 3,461,163 (1969); and U.S. Pat. No. 3,472,740 (1969).

A better understanding of the present invention will be had by reference to the following examples of specific embodiments of the present invention:

EXAMPLE I

A formulation of a shampoo and hair conditioner was produced by admixing 25 grams of polydimethyldiallyl ammonium chloride (40% activity) and 15 grams of hydroxyethyl cellulose in 1000 grams of water to make up approximately a one liter solution. The pH of the solution was adjusted with acetic acid to pH 5.6. The formulation thus produced had a viscosity of about 1400 cps at 100° F. The formulation was used in the manner of a conventional shampoo. The hair of a person was thoroughly wet, then the formulation was applied in sufficient quantity (approximately 16 ml.) to achieve a "lather sensation". The formulation was thereafter thoroughly massaged into the hair and scalp and, next, the hair was completely rinsed. The procedure was repeated once. Cleaning activity was demonstrated by the fact that the formulation removed the excess oil from the hair and scalp.

EXAMPLE II 0.5 grams of VASELINE white petroleum jelly was thoroughly massaged into the hair and scalp of a human test subject before shampooing. The hair obviously appeared "greasy" and matted down and felt heavy, thick, and oily. The hair was then shampooed with the base alone, namely, 15 grams hydroxyethyl cellulose in 1000 gms of water without any cationic organic polyelectrolytes. There was no appreciable change in the condition of the hair. When, however, 25 grams of the cationic organic polyelectrolyte, polydimethyldiallyl ammonium chloride (40% active), was added to this base, and the hair shampooed and rinsed, the excess oil was then, substantially completely removed from the hair leaving the hair "squeeky clean" easy to comb, manageable and with a natural luster.

EXAMPLE III

To determine water clarifying properties of this invention, a recirculated water system was set up containing about 400 gallons of water in a container. The water was continuously filtered through a cartridge filter commonly used for this purpose. Water clarity was determined by visual appearance e.g., the ability to see the fine texture on the bottom of the container. The system contained an air injection venturi at four separate locations so the return water could be and was aerated. Also an air blower forced air through holes in the bottom to rise to the surface. In effect the system set up was a typical spa.

The spa pH was maintained at 7.2 to 7.8 and the water superchlorinated daily to 5 ppm chlorine. The temperature was set at 100° F. and make-up water was added as necessary. (This is standard care and maintenance for a spa.) This spa was set up for for 50 days continuous operations with a minimum of 2 complete shampoo tests daily, using the procedure of Example I. The water remained crystal-clear for the entire duration. No foam resulted from the extensive use of the formulation, nor did the filter ever clog or need cleaning. Most of the washed out complex of polymer, dirt, and oil immediately rose to the surface of the water and was deposited along the edges of the spa. The accumulation was removed with a moist cloth or sponge.

In the preferred compositions or formulations of my shampoo, the organic cationic electrolyte is selected from one or more of the compounds listed in Table I, below.

TABLE I

Polydimethyldiallylammonium chloride
Copolymer of dimethyldiallylammonium chloride and acrylamide
Copolymer of dimethyldiallylammonium chloride and diacetone acrylamide
Poly(dimethylaminoethylmethyl acrylate)
Poly(dimethylaminopropylacrylate)
Dimethylaminopropylacrylate
Acrylamide(beta-methacryloyloxyethyl) trimethyl ammonium methyl sulfate
Copolymer acrylamide diallyl(beta-carbamoethyl)-ammonium chloride
Poly-2-hydroxy-3-(methacrylyoxy)propyltrimethyl ammonium chloride
Poly-beta-asparaginepolyalkylenepolyamine halohydrin resin
Polyamide-epichlorohydrin
Polyvinyl pyridine hydrochloride
N-(2,3-epoxy-1-propyl)-morpholine
Methyl-beta-propionamidodiallyl ammonium chloride Preferably hydroxyethyl cellulose is employed as a thickening agent and a weak organic acid, such as acetic acid or citric acid, is employed to adjust the pH down to between about pH 3.5 and about pH 6.5. A weak alkali or base can be used to adjust the pH up. A pH for the resulting composition of about pH 5.6 is preferable.

The organic cationic electrolyte should constitute about 1 part, by weight; the hydroxyethyl cellulose, about two parts, by weight; and the water, about 100 parts, by weight. The resulting viscosity should preferably be about 1600 cps.

The usual filters, employed for filtering the water in pools, spas or hot tubs, such as filter cartridges, diatomaceous earth and/or sand are not adversely effected by my formulations.

I claim:

1. A process of cleaning the hair of a person in a pool, spa or hot tub containing water and removing the resulting material from the water comprising:

(a) applying to the hair of a person disposed in a water pool, spa or hot tub in which water is recirculated, an organic water soluble cationic polyelectrolyte solution having a viscosity of above about 100 cps for collecting dirt and oil from said hair in said solution;
   (b) thereafter, rinsing said hair in the water of said pool, spa or tub; and
   (c) then separating from said water, a portion of said polyelectrolyte and dirt and oil collected as a flocculent from said water.

2. The process defined in claim 1 wherein said solution includes a thickening agent.

3. The process defined in claim 2 wherein the pH of said solution is from about 3.5 to about 6.5.

4. The process defined in claim 2 wherein said polyelectrolyte is a water soluble compound selected from the group consisting of amino and quaternary ammonium homopolymers and copolymers derived from dimethyl diallyl ammonium salts, said amino and quaternary homopolymers and copolymers each having an average molecular weight of between about 20,000 and about 3,000,000 and having a molecular chain containing one of the following formulas:

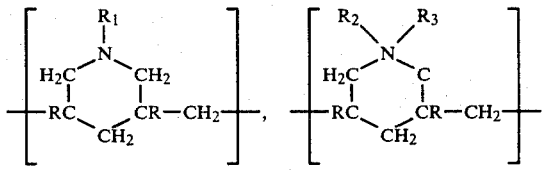

wherein R is selected from the group consisting of hydrogen and methyl; $R_1$ is selected from the group consisting of hydrogen, an alkyl group having one to 22 carbon atoms, a lower hydroxyalkl group having one to five carbon atoms, and a lower alkyl group containing a terminal amido group; and where $R_2$ and $R_3$ are respectively selected from the group consisting of alkyl groups having one to 22 carbon atoms, lower hydroxyalkyl groups having one to five carbon atoms, lower alkyl groups containing terminal amido groups; and wherein $R_2$ and $R_3$ together with N form piperidinyl or morphinyl groups.

* * * * *